(12) United States Patent
Ryan

(10) Patent No.: US 8,778,011 B2
(45) Date of Patent: Jul. 15, 2014

(54) SOFT CROWNS

(75) Inventor: Michael Ryan, Limerick (IE)

(73) Assignee: Cook Medical Technologies LLC, Bloomington, IN (US)

( * ) Notice: Subject to any disclaimer, the term of this patent is extended or adjusted under 35 U.S.C. 154(b) by 19 days.

(21) Appl. No.: 13/230,186

(22) Filed: Sep. 12, 2011

(65) Prior Publication Data

US 2012/0083871 A1    Apr. 5, 2012

Related U.S. Application Data

(60) Provisional application No. 61/388,236, filed on Sep. 30, 2010.

(51) Int. Cl.
*A61F 2/82* (2013.01)

(52) U.S. Cl.
USPC .......................................... 623/1.15; 623/1.53

(58) Field of Classification Search
USPC ............... 623/1.15, 1.31, 1.51, 1.53; 604/527
See application file for complete search history.

(56) References Cited

U.S. PATENT DOCUMENTS

| | | | |
|---|---|---|---|
| 6,585,758 B1 | 7/2003 | Chouinard et al. | |
| 6,976,993 B2 * | 12/2005 | Schaldach et al. | 623/1.15 |
| 7,001,425 B2 * | 2/2006 | McCullagh et al. | 623/1.53 |
| 7,029,494 B2 * | 4/2006 | Soun et al. | 623/1.15 |
| 7,670,367 B1 | 3/2010 | Chouinard et al. | |
| 2003/0149473 A1 | 8/2003 | Chouinard et al. | |
| 2005/0049682 A1 * | 3/2005 | Leanna et al. | 623/1.15 |
| 2007/0106370 A1 | 5/2007 | Chouinard et al. | |
| 2010/0274346 A1 | 10/2010 | Chouinard et al. | |
| 2011/0230957 A1 * | 9/2011 | Bonsignore et al. | 623/1.16 |

FOREIGN PATENT DOCUMENTS

| | | |
|---|---|---|
| WO | WO 01/35864 A1 | 5/2001 |
| WO | WO 2006/053270 A2 | 5/2006 |

OTHER PUBLICATIONS

Notification of Transmittal of the International Search Report and the Written Opinion of the International Searching Authority, or the Declaration, dated Dec. 7, 2011, for PCT/US2011/051179, 5p.

* cited by examiner

*Primary Examiner* — David Isabella
*Assistant Examiner* — Dinah Baria
(74) *Attorney, Agent, or Firm* — Brinks Gilson & Lione

(57) ABSTRACT

Soft crowns are provided for use in a medical device. Soft crowns may reduce the incidence of tissue perforations as a medical device engages a luminal wall. In certain embodiments, a soft crown may include a first strut and a second strut interconnected by an end portion. The end portion may include a third strut and a fourth strut that intersect to form a distal end of the soft crown. The first strut and the second strut may intersect other struts in the medical device to attach the crown thereto. The soft crown may bend or pivot about a plane defined by the intersections of the first strut and the second strut to the medical device.

6 Claims, 2 Drawing Sheets

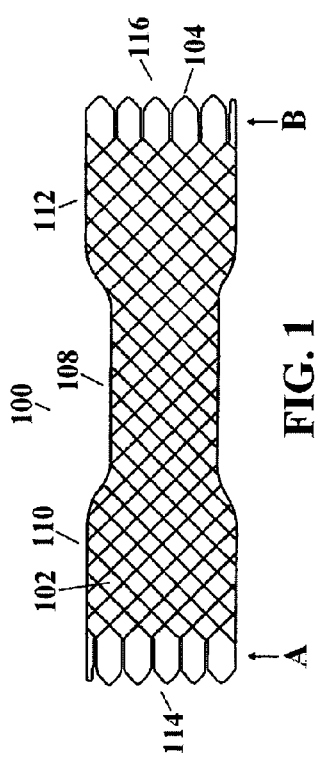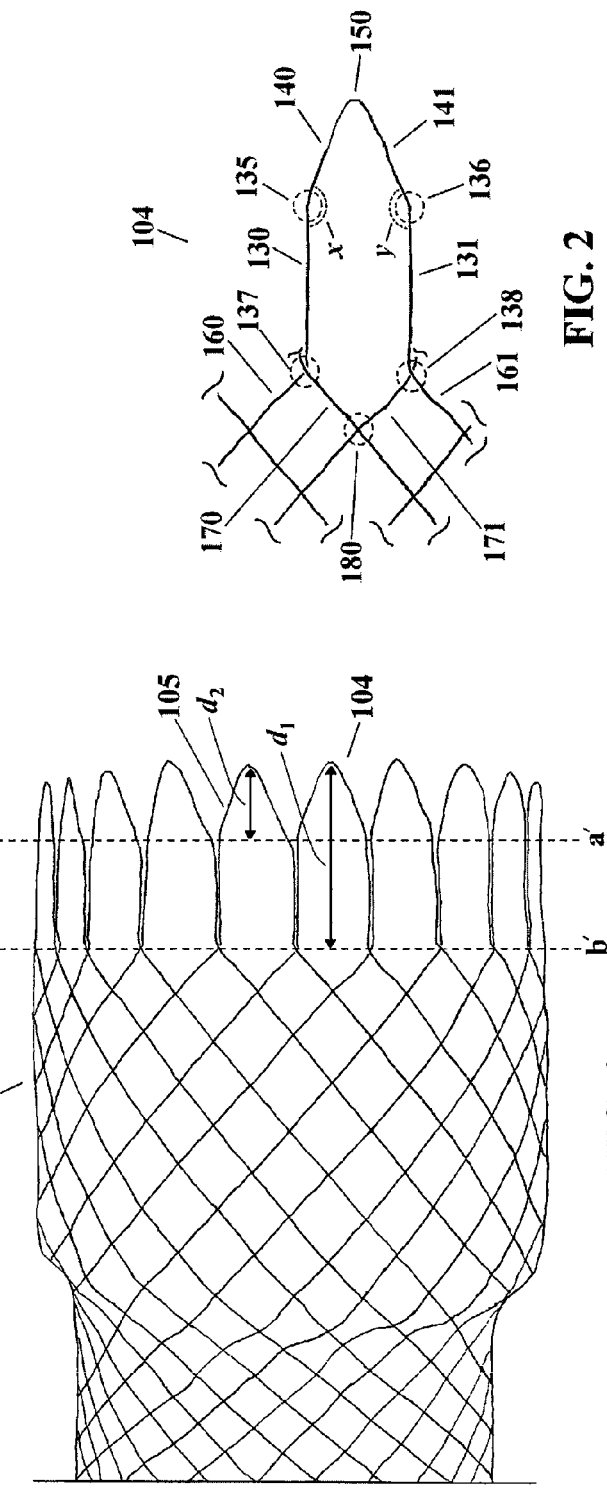

SOFT CROWNS

RELATED APPLICATION

The present patent document claims priority to, the benefit of the filing date, and all other benefits under 35 U.S.C. §119(e) and all other applicable statutes of U.S. Provisional Patent Application Ser. No. 61/388,236 filed Sep. 30, 2010, which is hereby incorporated by reference in its entirety.

TECHNICAL FIELD

The present disclosure relates generally to medical devices, and more particularly to stents having soft crowns.

BACKGROUND

Stents are medical devices commonly used to maintain patency of diseased body vessels, such as those of the vascular and gastrointestinal systems. Stents are often delivered via a minimally invasive procedure and thereafter expanded to contact and support the inner wall of the targeted vessel. In general, most stents include a tubular shaped support structure having a plurality of interstices configured to facilitate compression and expansion of the stent.

Many stents include proximal and distal flanges or flared ends to prevent stent migration subsequent to implantation. Flanges or flares are typically set to a larger expanded diameter relative to the stent central portion and may exert a higher radial force per unit area against the vessel wall, thereby securing the stent in position. One problem with these features, however, is that the flanges or flares can damage the vessel wall if they are excessively rigid. Specifically, the crowns at the end of a flange or flare can cause perforations as the luminal wall engages the stent during peristalsis. The resulting tissue perforations may be painful and can lead to more serious complications including infection, hemorrhage, and possibly death.

Accordingly, what is needed is a stent that can apply a high radial force to maintain lumen patency and prevent migration but can also flex in response to changes in lumen shape so as to reduce the incidence of tissue perforations and pain to a patient. In particular, what is needed is a stent having soft, flexible crowns.

SUMMARY

The present disclosure generally provides soft crowns. The crowns are configured to bend or yield to adapt to a patient anatomy and to reduce the incidence of tissue perforations to a vessel wall. The soft crowns may move or pivot independent of adjacent crowns in a medical device, thereby further reducing the rigidity of the end of such a device.

Accordingly, in one aspect, a crown of an implantable medical device is provided. The crown includes first and second struts, each strut having a proximal end and a distal end. The crown further includes an end portion having a first proximal end, a second proximal end, and a distal end. The first strut distal end intersects the first proximal end of the end portion. The second strut distal end intersects the second proximal end of the end portion. The first strut proximal end and the second strut proximal end together define a radial plane oriented perpendicular to the central longitudinal axis of the implantable medical device. The crown can bend or pivot about the plane independent of adjacent crowns in the implantable medical device.

In certain embodiments, the first and second struts may be substantially parallel to each other. The first and second struts may also be substantially parallel to the central longitudinal axis of the implantable medical device. Alternatively, the first and second struts may be aligned at an obtuse or acute angle relative to the central longitudinal axis. The first and second struts may be aligned with a helix angle of the implantable medical device.

In certain embodiments, the first strut includes a first strut central portion located between the first strut proximal end and the first strut distal end, wherein the first strut does not intersect or cross over or under other struts from adjacent crowns at the first strut central portion or the first strut distal end. Similarly, the second strut may include a second strut central portion located between the second strut proximal end and the second strut distal end, wherein the second strut does not intersect or cross over or under other struts from adjacent crowns at the second strut central portion or the second strut distal end.

In certain embodiments, the end portion may include a third strut and a fourth strut. The third strut includes the first proximal end of the end portion; and the fourth strut includes the second proximal end of the end portion. The third and fourth struts intersect to form the distal end of the end portion. Preferably, the intersections of the first strut and third strut, the second strut and the fourth strut, and the third strut and fourth strut create an atraumatically shaped bend at each intersection.

In certain embodiments, the crown may include fifth, sixth, seventh, and eighth struts. The first strut crosses the fifth strut and intersects the sixth strut, both the crossing and the intersection of said struts occurring at the first strut proximal end. The second strut crosses the seventh strut and intersects the eighth strut, both the crossing and the intersection of said struts occurring at the second strut proximal end.

In certain embodiments, the implantable medical device may be a stent. The stent may include a central portion and one or more flanges that include one or more of the crowns as described.

In another aspect, a braided stent is provided having a braided portion integral with a non-braided portion. The non-braided portion may comprise the crown of a stent, wherein the crown is configured to be flexible and atraumatic to a vessel wall. The non-braided portion includes a first strut and a second strut, wherein the first strut and the second strut intersect to form an apex. The first strut is separated from the braided portion by a third strut interconnecting the first strut to the braided portion. The second strut is separated from the braided portion by a fourth strut interconnecting the second strut to the braided portion. In certain embodiments, the third and the fourth struts may be substantially parallel to each other. The third and fourth struts may extend substantially parallel to the central longitudinal axis of the braided stent. Alternatively, the third and fourth struts may extend at an angle acute or obtuse relative to the central longitudinal axis. The third and fourth struts may extend at an angle aligned with a helix angle of the braided portion.

In certain embodiments, the interconnection points of the third and fourth struts to the braided portion may define a radial plane oriented perpendicular to the central longitudinal axis such that the third and fourth struts are pivotable about the radial plane in an abluminal or luminal direction.

In certain embodiments, the stent may include a flange wherein the flange end includes a non-braided portion as described. Optionally, one or both of the braided and non-braided portions may be coated with a membrane material.

In another aspect, an expandable stent for implantation in a body lumen is provided. The stent includes a tubular framework including a plurality of cells arranged into circumferential rows along a longitudinal axis of the stent. The stent further includes at least one cell located at an end of the stent that includes a proximal end and a distal end. The cell further includes a first strut and a second strut that intersect to form the distal end of the cell. The cell further includes a third strut that intersects the first strut. From the intersection with the first strut, the third strut extends in a proximally oriented direction. The cell further includes a fourth strut that intersects the second strut. From the intersection with the second strut, the fourth strut extends in a proximally oriented direction. The cell further includes a fifth strut that crosses over the third strut; and a sixth strut that crosses over the fourth strut. The fifth strut and the sixth strut cross each other to form the proximal end of the cell. The intersections of the first and second struts, the third and first struts, and the fourth and second struts create atraumatically shaped bends in the cell. The cell may bend or pivot about a plane defined by the points where the fifth strut crosses the third strut and the sixth strut crosses the fourth strut.

In certain embodiments, the third and fourth struts may be substantially parallel. The third and fourth struts may be aligned with the longitudinal axis of the tubular framework. Alternatively, the third and fourth struts may be aligned with an angle obtuse or acute relative to the central longitudinal axis of the tubular framework. The third and fourth struts may be aligned with a helix angle of the tubular framework where the tubular framework includes one or more helically wound filaments having at least one helix angle.

Other devices, systems, methods, features and advantages will be, or will become, apparent to one with skill in the art upon examination of the following figures and detailed description. It is intended that all such additional devices, systems, methods, features and advantages be included within this description, and be protected by the following claims.

BRIEF DESCRIPTION OF THE DRAWINGS

The system may be better understood with reference to the following drawings and description. The components in the figures are not necessarily to scale, with emphasis instead being placed upon illustrating the principles of the present disclosure. Moreover, in the figures, like referenced numerals designate corresponding parts throughout the different views.

FIG. 1 depicts a side-view of a stent including soft crowns.
FIG. 2 depicts a side-view of a soft crown.
FIG. 3 depicts a side-view of a flange including soft crowns.

DETAILED DESCRIPTION

Definitions

Figure 4:
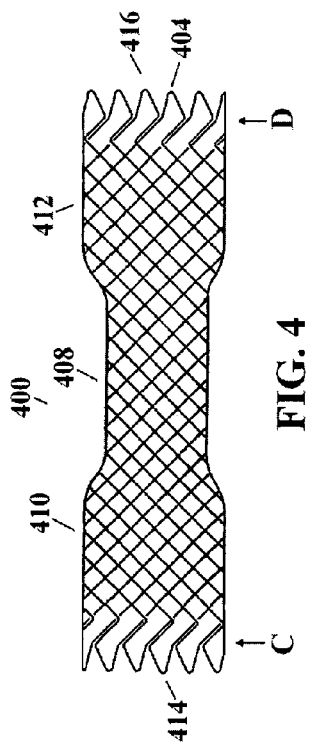
FIG. 4 depicts a side-view of a stent including soft crowns.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The present disclosure also contemplates other embodiments "comprising," "consisting of" and "consisting essentially of," the embodiments or elements presented herein, whether explicitly set forth or not.

The term "proximal," as used herein, refers to a direction that is generally towards a physician during a medical procedure.

The term "distal," as used herein, refers to a direction that is generally towards a target site within a patient's anatomy during a medical procedure.

The term "biocompatible," as used herein, refers to a material that is substantially non-toxic in the in vivo environment of its intended use, and that is not substantially rejected by the patient's physiological system. A biocompatible structure or material, when introduced into a majority of patients, will not cause an undesirably adverse, long-lived or escalating biological reaction or response. Such a response is distinguished from a mild, transient inflammation which typically accompanies surgery or implantation of foreign objects into a living organism.

Devices and Systems

FIGS. 1-3 depict a first illustrative embodiment of a stent 100 having soft crowns. The stent structure is formed from one or more of uniform wires helically wound in an under-over-under configuration. Cross points in the structure (i.e., where the wire crosses over and under itself) form a plurality of rhombus shaped cells (e.g., cell 102) defined at their perimeter by the wire. Cells located at the proximal and distal ends of the stent include crowns at their respective ends (e.g., crown 104). The stent framework includes a tubular shaped central body portion 108 extending longitudinally between a proximal flange 110 and a distal flange 112. The flanges include circumferential rows of crowns A and B located, respectively, at proximal end 114 and distal end 116. As will be described in greater detail below, the crowns are configured to reduce the incidence of tissue perforations and pain to a patient, and in addition, to make the stent more adaptive to peristaltic motion.

FIG. 2 shows an enlarged side-view of crown 104. The crown includes two apex struts 140 and 141 that intersect to form an atraumatically shaped crown apex 150 located at distal end 116. From the crown apex, apex strut 140 extends at a first angle x to intersect longitudinal strut 130 at a bend 135; and apex strut 141 extends at a second angle y to intersect longitudinal strut 131 at a bend 136. From bend 135 longitudinal strut 130 extends proximally to intersect woven strut 160 at cross point 137; and similarly, longitudinal strut 131 extends proximally from bend 136 to intersect woven strut 161 at cross point 138. The longitudinal struts extend proximally from the apex struts to connect the apex struts to the stent framework. The longitudinal struts and the apex struts are formed from a continuous segment of wire, with bends in the wire differentiating the struts. Woven struts 160 and 161 continue to extend into the weave pattern as part of the helical weave, interconnecting with other woven struts therein. In addition to bending at cross points 137 and 138 to intersect woven struts 160 and 161, the segment of wire forming the apex and longitudinal struts crosses under and over other struts in the stent framework at said points. Specifically, longitudinal strut 130 crosses under woven strut 170 at cross point 137; and longitudinal strut 131 crosses over woven strut 171 at cross point 138. Woven struts 170 and 171 cross one another at cross point 180, each also interconnecting with other woven struts at this cross point. Thus, the woven struts 170 and 171 form the back (i.e., proximal) perimeter of the cell that includes crown 104.

FIG. 3 shows that the crown cross points (e.g., see FIG. 2, points 137 and 138) in flange 112 together define a plane b-b' extending radially through the stent, wherein the plane is perpendicular to the central longitudinal axis of the stent. From plane b-b' to the crown apexes, the crowns are free from the weave framework and therefore may move independently from one another in response to an external force (e.g., crowns 104 and 105 may move independently). The crowns may also independently bend or flex about radially oriented plane a-a' defined by intersections of the longitudinal struts and the apex struts (e.g., see FIG. 2, points 135 and 136). Thus, one or more crowns of stent 100 may bend inward toward the luminal space or outward toward the abluminal space, pivoting at the cross points and/or the bend points (e.g., crown 104 may bend about points 135 and 136; and/or 137 and 138). The flexibility of the crowns may be further increased by increasing the length of the apex struts and/or the longitudinal struts. The additional length provided by the longitudinal struts may allow the crowns to better adapt to changes in lumen shape, which in turn can reduce the incidence of tissue perforations and pain to a patient. With reference again to FIG. 3, the longitudinal distance from the crown apex to plane b-b' is shown as distance $d_1$; and the longitudinal distance from the crown apex to plane a-a' is shown as distance $d_2$. As depicted, $d_1$ is greater than $d_2$, but each can be varied as appropriate to provide a crown with a desired flexibility profile. Accordingly, the first and second angles x and y of the apex struts may also be varied as appropriate. In one preferred embodiment, the flexibility of a crown may be increased by increasing the magnitude of $d_1$ while keeping $d_2$ constant.

Figure 5:
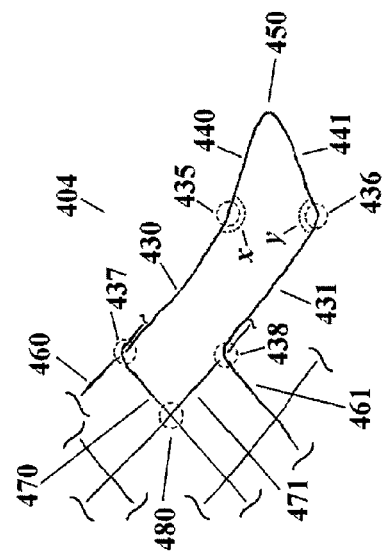
FIG. 5 depicts a side-view of a soft crown.
Figure 6:
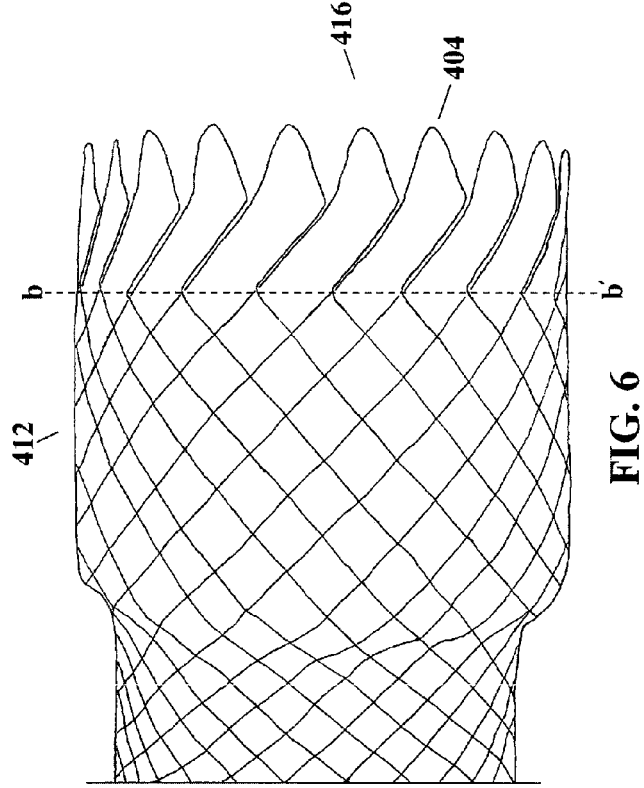
FIG. 6 depicts a side-view of a flange including soft crowns.

FIGS. 4-6 show another illustrative embodiment of a stent having soft crowns. FIG. 4 shows a woven stent 400 formed from a single strand of uniform wire helically wound in an under-over-under configuration, similar to that of stent 100. Stent 400 includes a tubular central body portion 408 extending longitudinally between a proximal flange 410 and a distal flange 412. Proximal flange 410 includes a circumferential row C of crowns at proximal end 414; and distal flange 412 includes a circumferential row D of crowns (e.g., crown 404) located at distal end 416.

FIG. 5 shows an enlarged side-view of crown 404. The crown includes two apex struts 440 and 441 that intersect at the distal end to form an atraumatically shaped crown apex 450. From the crown apex, apex strut 440 extends at a first angle x to intersect angular strut 430 at a bend 435; and apex strut 441 extends at a second angle y to intersect angular strut 431 at a bend 436. The angular struts and the apex struts are formed from a single segment of wire, with bends in the wire differentiating the struts. From bend 435 angular strut 430 extends to intersect woven strut 460 at cross point 437; and similarly, angular strut 431 extends from bend 436 to intersect woven strut 461 at cross point 438. As depicted, the angular struts 430 and 431 are aligned with struts in the weave pattern, such as woven strut 460. In other words, relative to the central longitudinal axis the angular struts are on the same helix angle as woven strut 460, among others. After intersection with the angular struts, woven struts 460 and 461 continue to extend into the weave pattern as part of the helical weave, interconnecting with other woven struts therein. In addition to intersecting woven struts 460 and 461 at cross points 437 and 438, the segment of wire forming the apex and angular struts crosses under and over other struts in the stent framework at said points. Specifically, angular strut 430 crosses under woven strut 470 at cross point 437; and angular strut 431 crosses over woven strut 471 at cross point 438. Woven struts 470 and 471 cross over one another at cross point 480, each also interconnecting with other woven struts at this cross point. Thus, the woven struts 470 and 471 form the back (i.e., proximal) perimeter of the cell that includes crown 404.

FIG. 6 shows an enlarged side-view of flange 412 including crown 404. Similar to flange 112, the crown cross points define a radial plane b-b' oriented perpendicular to the stent's central longitudinal axis. From line b-b' to distal end 416 of the stent, the crowns are free from the weave pattern, and therefore may move independently from one another in response to an external force. The crowns may also bend or flex at the various intersections of struts in the crowns, thereby providing additional degrees of motion and flexibility in the crown relative to those of a conventional stent.

The structural elements forming the crowns may be of any suitable dimensions. Depending on the type of stent, its size, and intended use, the longitudinal, angular, and apex struts may vary in length as appropriate to provide a crown of desired flexibility. Accordingly, several configurations of soft crowns are possible. In general however, the longitudinal struts independently range from about 3 mm to about 15 mm in length. The angular struts independently range from about 2 mm to about 20 mm in length. The apex struts independently range from about 2 mm to about 10 mm in length. The first and second angles x and y may vary as appropriate to provide a crown apex of suitable shape. In general, the angles independently range from about 100 degrees to about 260 degrees. In accordance with the first illustrative embodiment (FIGS. 1-3), angles x and y generally range from about 120 degrees to about 170 degrees. In accordance with the second illustrative embodiment (FIGS. 4-6), angle x generally ranges from about 190 degrees to about 230 degrees; and angle y generally ranges from about 110 degrees to about 150 degrees. In certain embodiments, each of the longitudinal struts may be of the same length or about the same length. In other embodiments, the longitudinal struts may be fabricated to different lengths to provide crowns of different shapes and flexibility profiles. Similarly, each of the angular struts may be of the same length, or alternatively, may vary in length. Similarly, each of the apex struts may be of the same length, or alternatively, may vary in length.

In certain embodiments, a stent according to the present disclosure may include soft crowns on one or both ends of the stent. For example, a stent may include conventional crowns on a distal flange and soft crowns on a proximal flange, or vice versa. A stent may include alternative configurations of soft crowns on each respective end. For example, in certain embodiments a stent may include the soft crowns as disclosed in FIGS. 1-3 on one flange and the soft crowns as disclosed in FIGS. 4-6 on the other flange.

A stent according to the present disclosure may have any suitable braid angle. The radial force of the stent may be controlled by adjusting the braid angle accordingly. Stents with higher braid angles typically exert greater radial force and exhibit greater foreshortening during expansion from a compressed state. Stents with lower braid angles typically exert lower radial force and experience less foreshortening upon expansion. In some instances, if the stent is partially or fully covered with a membrane material, the braid angle can be lowered because membrane coverings typically add rigidity to the stent structure. In addition to adjusting the braid angle, the radial force of the stent can be adjusted through selection of particular materials as well as the shape and size of the filaments or wires forming the stent structure.

Although the illustrated embodiments depict a stent having a central body portion and two flanges, other stent configurations are possible. For example, a stent may include a single flange, two asymmetrically shaped flanges, or may entirely lack flanges and instead have a uniform or substantially uniform diameter along the entire length of the stent. A stent may include a uniform diameter along the length of the stent but include slightly flared proximal and/or distal ends. The central body portion may smoothly transition to a flange or flare, or alternatively, may progressively step up in diameter to a flange or flare. Generally, a stent may be implanted in a vessel (e.g., esophagus, duodenum, colon, trachea, or the like) such that the central body portion engages a diseased area and the flanges or ends engage healthy tissue adjacent the diseased area. Preferably, the flanges are configured to anchor the stent at the site of implantation, thereby reducing the incidence of proximal and distal migration. Preferably, the flanges are sized and shaped to accommodate the vessel or organ of implantation. For example, stents destined for lower esophageal implantation may have differently shaped and sized flanges compared to a stent designed for upper esophageal implantation. In addition to the soft crowns, the flanges may include other features or configurations designed to reduce incidence of tissue perforation and overgrowth. For example, the ends (e.g., the crown cells) of the flanges may curve or bend inward toward the stent lumen to minimize tissue damage at or near the stent ends. In certain embodiments, a stent may include other design elements configured to secure the stent at the site of implantation. For example, in certain embodiments, a stent may include small anchors, clips, hooks, or barbs that will anchor the stent to the internal wall of the targeted body lumen. In other embodiments, the stent may be sutured to the site of implantation at one or more portions of the stent structure.

A stent including soft crowns may include one or more components configured to aid in visualization and/or adjustment of the stent during implantation, repositioning, or retrieval. For example, a stent may include one or more radiopaque markers configured to provide for fluoroscopic visualization for accurate deployment and positioning. Radiopaque markers may be affixed (e.g., by welding, gluing, suturing, or the like) at or near the ends of the stent at a cross point of filament(s) in the braid pattern. In certain embodiments, a stent may include four radiopaque markers with two markers affixed to a first flange and two to a second flange. Optionally, radiopacity can be added to a stent through coating processes such as sputtering, plating, or co-drawing gold or similar heavy metals onto the stent. Radiopacity can also be included by alloy addition. Radiopaque materials and markers may be comprised of any suitable biocompatible materials, such as tungsten, tantalum, molybdenum, platinum, gold, zirconium oxide, barium salt, bismuth salt, hafnium, and/or bismuth subcarbonate.

A stent including soft crowns may include one or more loops, lassos, or sutures on the stent structure to facilitate repositioning or removal of the stent during or after implantation. For example, a stent may include a loop at or near the proximal end of the stent. The loop material may circumscribe the flange and in certain embodiments may be wound through the absolute end cells to affix the loop to the stent. The loop may comprise any appropriate biocompatible material, such as for example, suture materials or other polymeric or metallic materials such as polyethylene, ultra-high molecular weight polyethylene, polyester, nylon, stainless steel, nitinol, or the like. Optionally, the lasso may be coated with a material, such as polytetrafluoroethylene, to reduce frictional interactions of the lasso with surrounding tissue.

Stents including soft crowns may be self-expanding, mechanically expandable, or a combination thereof. Self-expanding stents may be self-expanding under their inherent resilience or may be heat activated wherein the stent self-expands upon reaching a predetermined temperature or range of temperatures. One advantage of self-expanding stents is that traumas from external sources or natural changes in the shape of a body lumen do not permanently deform the stent. Thus, self-expanding stents may be preferred for use in vessels that are subject to changes in shape and/or changes in position, such as those of the peripheral and gastrointestinal systems. Peripheral vessels regularly change shape as the vessels experience trauma from external sources (e.g., impacts to arms, legs, etc.); and many gastrointestinal vessels naturally change shape as peristaltic motion advances food through the digestive tract. One common procedure for implanting a self-expanding stent involves a two-step process. First, if necessary, the diseased vessel may be dilated with a balloon or other device. The stent may be loaded within a sheath that retains the stent in a compressed state for delivery to the targeted vessel. The stent may then be guided to the target anatomy via a delivery catheter and thereafter released by retracting or removing the retaining sheath. Once released from the sheath, the stent may radially expand until it contacts and presses against the vessel wall. In some procedures, self-expanding stents may be delivered with the assistance of an endoscope and/or a fluoroscope. An endoscope provides visualization as well as working channels through which devices and instruments may be delivered to the site of implantation. A fluoroscope also provides visualization of the patient anatomy to aid in placement of an implantable device, particularly in the gastrointestinal system.

Mechanically expandable stents (e.g., balloon expandable stents) having soft crowns may be made from plastically deformable materials (e.g., 316L stainless steel). A balloon-expandable stent may be crimped and delivered in a reduced diameter and thereafter expanded to a precise expanded diameter. Balloon expandable stents can be used to treat stenosed coronary arteries, among other vessels. One common procedure for implanting a balloon expandable stent involves mounting the stent circumferentially on a balloon-tipped catheter and threading the catheter through a vessel passageway to the target area. Once the balloon is positioned at the targeted area, the balloon may be inflated to dilate the vessel and radially expand the stent. The balloon may then be deflated and removed from the passageway.

Expandable stents according to the present disclosure may be formed by any suitable method as is known in the art. In certain embodiments, the expandable stents may be fabricated by braiding, weaving, knitting, crocheting, welding, suturing, or otherwise machining together one or more filaments or wires into a tubular frame. Such stents may be referred to as braided, woven, or mesh stents. A braided stent may be fabricated by, for example, use of a braiding mandrel having specifically designed features (e.g., grooves and detents) for creating such a stent. A variety of braiding patterns are possible, such as for example, one-under and one-over patterns or two-under and two-over patterns. The filaments or wires may be of various cross-sectional shapes. For example, the filaments or wires may be flat in shape or may have a circular-shaped cross-section. The filaments or wires may have any suitable diameter, such as for example, from about 0.10 to about 0.30 mm. As will be described in greater detail below, the expandable stents may formed from a variety of biocompatible materials. For example, the filaments or wires may comprise one or more elastically deformable materials such as shape memory alloys (e.g., 304 stainless steel, nitinol, and the like).

Alternatively, the expandable stents may be formed from metallic or polymeric sheets or tubular blanks. For example, a stent framework comprising a selected pattern of struts defining a plurality of cells or interstices may be fabricated by subjecting a metallic or polymeric sheet or tubular blank to laser cutting, chemical etching, high-pressure water etching, mechanical cutting, cold stamping, and/or electro discharge machining. After obtaining a sheet of cut, etched or machined material with the appropriate strut pattern, the sheet may be rolled into a tubular shape to form the stent framework. The stent framework may also be machined from a tubular blank, thereby eliminating the need for a rolling step.

A stent including soft crowns may be made from any suitable biocompatible material(s). For example, a stent may include materials such as stainless steel, nitinol, MP35N, gold, tantalum, platinum or platinum iridium, niobium, tungsten, iconel, ceramic, nickel, titanium, stainless steel/titanium composite, cobalt, chromium, cobalt/chromium alloys, magnesium, aluminum, or other biocompatible metals and or composites or alloys. Examples of other materials that may be used to form stents include carbon or carbon fiber; cellulose acetate, cellulose nitrate, silicone, polyethylene terephthalate, polyurethane, polyamide, polyester, polyorthoester, polyanhydride, polyether sulfone, polycarbonate, polypropylene, ultra high molecular weight polyethylene, polytetrafluoroethylene, or another biocompatible polymeric material, or mixtures or copolymers of these; polylactic acid, polyglycolic acid or copolymers thereof; a polyanhydride, polycaprolactone, polyhydroxybutyrate valerate or another biodegradable polymer, or mixtures or copolymers of these; a protein, an extracellular matrix component, collagen, fibrin, or another biologic agent; or a suitable mixture of any of these.

A stent including soft crowns may be fabricated to any suitable dimensions. A stent having a particular length and diameter may be selected based on the targeted vessel. For example, a stent designed for esophageal implantation may have a length ranging from about 5 cm to about 15 cm and a body diameter of about 15 mm to about 25 mm. Optionally, an esophageal stent may include one or more flanges or flares of about 10 mm to about 25 mm in length and about 20 mm to about 30 mm in diameter. A stent designed for colon implantation may have a length ranging from about 5 cm to about 15 cm and a body diameter of about 20 mm to about 25 mm. Optionally, a colonic stent may include one or more flanges having a diameter of about 25 mm to about 35 mm.

In certain embodiments a stent with soft crowns may include a membrane covering over the stent framework. A stent may include covering over the entire stent framework from the proximal end to the distal end. Alternatively, the stent may have covering over a central portion of the structure but have uncovered ends or flanges. Where the stent flanges include a membrane covering, preferably the soft crowns lack membrane covering between other adjacent crowns so that the crowns may move independently from one another. Any suitable biocompatible material may be used as the membrane covering. Preferably, the membrane covering is an elastic or flexible material that can adapt to radial compression of a stent prior to delivery, as well as foreshortening of a stent during expansion from a compressed state. Suitable membrane materials include, for example, silicones (e.g. polysiloxanes and substituted polysiloxanes), polyurethanes, thermoplastic elastomers, polyolefin elastomers, polyethylene, polytetrafluoroethylene, nylon, and combinations thereof. In one preferred embodiment, the membrane covering comprises silicone. In certain embodiments, where the stent will be implanted at or near an acidic environment (e.g., will be exposed to gastric fluids), preferably the membrane covering is resistant to acid degradation.

The membrane covering may be applied to a stent by any suitable method as is known in the art. For example, the membrane may be applied by spraying, dipping, painting, brushing, or padding. Generally, the membrane covering or coating has a thickness ranging from about 0.0025 mm to about 2.5 mm, from about 0.01 mm to about 0.5 mm, or from about 0.03 mm to about 0.07 mm. The thickness of the membrane may be selected, for example, by controlling the number of dips or passes made during the application process. In one exemplary embodiment, a braided stent may be dipped in silicone liquid, removed, and thereafter cured. Preferably, the coating extends over the abluminal and luminal surfaces of the filaments, and also resides in the cells or interstices defined by the filament braid pattern.

In certain embodiments, a stent with soft crowns may include one or more bioactive agents coated on the stent surfaces. A bioactive agent may be applied directly on the surface of the stent (or on a primer layer which is placed directly on the surface of the stent). Alternatively, the bioactive agent may be mixed with a carrier material and this mixture applied to the stent. In such configuration, the release of the bioactive agent may be dependent on factors including composition, structure and thickness of the carrier material. The carrier material may contain pre-existing channels, through which the bioactive agent may diffuse, or channels created by the release of bioactive agent, or another soluble substance, from the carrier material.

One or more barrier layers may be deposited over the layer containing the bioactive agent. A combination of one or more layers of bioactive agent, mixtures of carrier material/bioactive, and barrier layers may be present. The bioactive agent may be mixed with a carrier material and coated onto the stent and then over coated with barrier layer(s). Multiple layers of bioactive agent, or mixtures of carrier material/bioactive, separated by barrier layers may be present to form a multi-coated stent. Different bioactive agents may be present in the different layers.

The carrier material and/or the barrier layer can include a bioelastomer, PLGA, PLA, PEG, Zein, or a hydrogel. In certain other embodiments, the carrier material and/or the barrier layer includes microcrystalline cellulose, hydroxypropylmethyl cellulose, hydroxypropyl cellulose, a cellulose product, a cellulose derivative, a polysaccharide or a polysaccharide derivative. The carrier material and/or barrier layer may include lactose, dextrose, mannitol, a derivative of lactose, dextrose, mannitol, starch or a starch derivative. The carrier material and/or barrier layer may include a biostable or a biodegradable material, for example, a biostable or biodegradable polymer.

A variety of bioactive agents may be applied to the stent in accordance with the intended use. For example, bioactive agents that may be applied include antiproliferative/antimitotic agents including natural products such as vinca alkaloids (vinblastine, vincristine, and vinorelbine), paclitaxel, rapamycin analogs, epidipodophyllotoxins (etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (for example, L-asparaginase which systemically metabolizes L-asparagine and deprives cells which do not have the capacity to synthesize their own asparagine); antiplatelet agents such as (GP) II b/IIIa inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives (cyclosporine, tacrolimus (FK-506), sirolimus (rapamycin), tacrolimus, everolimus, azathioprine, mycophenolate mofetil); angiogenic agents: vascular endothelial growth factor (VEGF), fibroblast growth factor (FGF); angiotensin receptor blockers; nitric oxide and nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; endothelial progenitor cells (EPC); angiopeptin; pimecrolimus; angiopeptin; HMG co-enzyme reductase inhibitors (statins); metalloproteinase inhibitors (batimastat); protease inhibitors; antibodies, such as EPC cell marker targets, CD34, CD133, and AC 133/CD133; Liposomal Biphosphate Compounds (BPs), Chlodronate, Alendronate, Oxygen Free Radical scavengers such as Tempamine and PEA/NO preserver compounds, and an inhibitor of matrix metalloproteinases, MMPI, such as Batimastat.

A bioactive agent may be applied, for example, by spraying, dipping, pouring, pumping, brushing, wiping, vacuum deposition, vapor deposition, plasma deposition, electrostatic deposition, ultrasonic deposition, epitaxial growth, electrochemical deposition or any other method known to the skilled artisan.

Prior to applying a membrane, and/or a bioactive agent, a stent may be polished, cleaned, and/or primed as is known in the art. A stent may be polished, for example, with an abrasive or by electropolishing. A stent may be cleaned by inserting the stent into various solvents, degreasers and cleansers to remove any debris, residues, or unwanted materials from the stent surfaces. Optionally, a primer coating may be applied to the stent prior to application of a membrane covering, bioactive, or other coating. Preferably, the primer coating is dried to eliminate or remove any volatile components. Excess liquid may be blown off prior to drying the primer coating, which may be done at room temperature or at elevated temperatures under dry nitrogen or other suitable environments including an environment of reduced pressure. A primer layer may comprise, for example, silane, acrylate polymer/copolymer, acrylate carboxyl and/or hydroxyl copolymer, polyvinylpyrrolidone/vinylacetate copolymer (PVP/VA), olefin acrylic acid copolymer, ethylene acrylic acid copolymer, epoxy polymer, polyethylene glycol, polyethylene oxide, polyvinylpyridine copolymers, polyamide polymers/copolymers polyimide polymers/copolymers, ethylene vinylacetate copolymer and/or polyether sulfones.

A stent according to the present disclosure may be delivered to a body lumen using various techniques. Generally, under the aid of endoscopic and/or fluoroscopic visualization a delivery device containing the stent is advanced into the vicinity of the target anatomy. The targeted lumen may be predilated with a balloon catheter or other dilation device, if necessary. Preferably, the stent is delivered in a compressed state in a low profile delivery device. This approach may reduce the risk of tissue perforations during delivery. Once the delivery device is in place, the stent may be released from the retaining sheath or the like. In one preferred embodiment, a stent may be delivered with a controlled release system (e.g., Evolution™ Controlled-Release Stent, Cook Endoscopy Inc., Winston-Salem, N.C.). A controlled release device permits the physician to slowly release the stent from the retaining sheath and in some instances, recapture the stent to allow for repositioning. After implantation, the delivery device and any other devices (e.g., wire guides, catheters, etc.) may be removed.

While various embodiments of the presently disclosed soft crowns have been described, it will be apparent to those of ordinary skill in the art that many more embodiments and implementations are possible within the scope of the present disclosure. Accordingly, the disclosure is not to be restricted except in light of the attached claims and their equivalents.

The invention claimed is:

1. An expandable stent for implantation in a body lumen comprising a circumferential row of cells located at an end of the stent, each cell comprising:
    a proximal end and a distal end;
    a first strut and a second strut, wherein the first and second struts intersect to form the distal end;
    a third strut that intersects the first strut and extends proximally therefrom;
    a fourth strut that intersects the second strut and extends proximally therefrom;
    a fifth strut that crosses over an abluminal surface of the third strut;
    a sixth strut that crosses under a luminal surface of the fourth strut,
    wherein the fifth strut and the sixth strut cross each other to form the proximal end, and wherein the cell may bend or pivot about a plane defined by the points where the fifth strut crosses over the third strut and the sixth strut crosses under the fourth strut.

2. The stent of claim 1, wherein the third and fourth struts are parallel to each other.

3. The stent of claim 1, wherein the third and fourth struts are aligned with a longitudinal axis of the stent.

4. The stent of claim 1, wherein the third and fourth struts are aligned with an angle obtuse or acute relative to a longitudinal axis of the stent.

5. The stent of claim 1, wherein the third and fourth struts are aligned with a helix angle of the stent.

6. The stent of claim 1, wherein the third strut of a first cell in the circumferential row intersects the sixth strut of a second cell in the circumferential row, and wherein the fourth strut of the first cell intersects the fifth strut of a third cell in the circumferential row.

* * * * *